US008581206B2

(12) United States Patent
Man et al.

(10) Patent No.: US 8,581,206 B2
(45) Date of Patent: Nov. 12, 2013

(54) FOCUSED ION BEAM SYSTEM AND SAMPLE PROCESSING METHOD USING THE SAME

(75) Inventors: Xin Man, Chiba (JP); Kouji Iwasaki, Chiba (JP); Junichi Tashiro, Chiba (JP)

(73) Assignee: SII Nanotechnology Inc. (JP)

( * ) Notice: Subject to any disclaimer, the term of this patent is extended or adjusted under 35 U.S.C. 154(b) by 210 days.

(21) Appl. No.: 12/707,024

(22) Filed: Feb. 17, 2010

(65) Prior Publication Data

US 2010/0213386 A1    Aug. 26, 2010

(30) Foreign Application Priority Data

Feb. 20, 2009    (JP) .................. 2009-037307

(51) Int. Cl.
*G21K 5/10*    (2006.01)
*G21K 5/08*    (2006.01)
*G21K 1/00*    (2006.01)
*G21K 5/04*    (2006.01)

(52) U.S. Cl.
USPC ............... 250/442.11; 250/309; 250/440.11; 250/492.3

(58) Field of Classification Search
USPC ............... 850/18, 8, 52; 250/400, 492.1, 306, 250/440.11, 442.11, 492.3, 309
See application file for complete search history.

(56) References Cited

U.S. PATENT DOCUMENTS

| 6,927,391 | B2 * | 8/2005 | Tokuda et al. ............... 850/10 |
| 7,849,515 | B2 * | 12/2010 | Hashiguchi et al. ............ 850/18 |
| 7,888,655 | B2 * | 2/2011 | van Gaasbeek et al. . 250/442.11 |
| 7,926,328 | B2 * | 4/2011 | Yasutake et al. ............... 73/105 |
| 2002/0079463 | A1 * | 6/2002 | Shichi et al. ............... 250/492.1 |
| 2004/0185586 | A1 * | 9/2004 | Yasutake et al. ............... 438/14 |
| 2004/0245466 | A1 * | 12/2004 | Robinson et al. ............. 250/311 |
| 2007/0063148 | A1 * | 3/2007 | Miyazaki et al. ........ 250/442.11 |
| 2008/0073535 | A1 | 3/2008 | Hong et al. |
| 2008/0073562 | A1 * | 3/2008 | Suzuki ..................... 250/440.11 |
| 2008/0099695 | A1 * | 5/2008 | Sugizaki ................... 250/492.1 |
| 2008/0135750 | A1 * | 6/2008 | Kley ............................. 250/306 |
| 2008/0258056 | A1 * | 10/2008 | Zaykova-Feldman et al. ........................... 250/307 |
| 2008/0302961 | A1 * | 12/2008 | Tashiro et al. ............... 250/310 |
| 2009/0008578 | A1 * | 1/2009 | Tomimatsu et al. ..... 250/492.21 |
| 2009/0114842 | A1 * | 5/2009 | Takahashi et al. ........ 250/442.11 |
| 2009/0119807 | A1 * | 5/2009 | Man et al. ........................ 850/18 |
| 2009/0126051 | A1 * | 5/2009 | Kagaya ........................ 850/18 |
| 2009/0188011 | A1 * | 7/2009 | Yasutake ........................ 850/52 |
| 2010/0032581 | A1 * | 2/2010 | Grosse et al. ............ 250/442.11 |
| 2010/0305747 | A1 * | 12/2010 | Agorio et al. ................ 700/213 |
| 2011/0017922 | A1 * | 1/2011 | Amador ................... 250/442.11 |
| 2011/0031397 | A1 * | 2/2011 | Zaykova-Feldman et al. ........................... 250/307 |

FOREIGN PATENT DOCUMENTS

| JP | 04-131751 U | 12/1992 |
| JP | 07-146224 A | 6/1995 |
| JP | 2003-065905 A | 3/2003 |
| JP | 2004-245660 A | 9/2004 |

(Continued)

*Primary Examiner* — David A Vanore
*Assistant Examiner* — Wyatt Stoffa
(74) *Attorney, Agent, or Firm* — Brinks Gilson & Lione

(57) ABSTRACT

A focused ion beam system includes a sample holder having a fixing plane for fixing a sample, a sample base on which the sample holder is provided, a focused ion beam irradiating mechanism that irradiates a focused ion beam to the sample, microtweezers that hold the sample and have the axial direction at a predetermined angle to a surface of the sample base, an opening/closing mechanism that opens and closes the microtweezers, a rotating mechanism that rotates the microtweezers about the axial direction, and a moving mechanism that moves the position of the microtweezers.

4 Claims, 16 Drawing Sheets

(56) References Cited

FOREIGN PATENT DOCUMENTS

| | | | |
|---|---|---|---|
| JP | 2005-205573 A | 8/2005 |
| JP | 2007-108105 A | 4/2007 |
| JP | 2008-026312 A | 2/2008 |
| JP | 2008-159294 A | 7/2008 |
| WO | WO 2008/051880 A2 | 5/2008 |

\* cited by examiner

FOCUSED ION BEAM SYSTEM AND SAMPLE PROCESSING METHOD USING THE SAME

RELATED APPLICATIONS

This application claims priority under 35 U.S.C. §119 to Japanese Patent Application No. 2009-037307 filed on Feb. 20, 2009, the entire content of which is hereby incorporated by reference.

BACKGROUND OF THE INVENTION

1. Field of the Invention

The present invention relates to a focused ion beam system that processes a sample by using focused ion beam, and a sample processing method using the same.

2. Description of the Related Art

Hitherto, focused ion beam systems have been used for, for example, performing etching processing on a semiconductor device to acquire a cross-section thereof for observation or processing a sample into a flake to produce a sample piece for a transmission electron microscope (TEM), which will be called TEM sample. The TEM sample is produced by removing both sides of an original sample by ion beam etching processing into a flake having an exposed cross-section to be observed. The flake may be moved by a manipulator having a probe (or needle), for example, to a sample holder for TEM observation to perform TEM observation. In this case, the needle is brought closer to the flake, and ion beam deposition is used to fix both of them, and the needle is manipulated to bring the flake closer to the sample holder. Then, ion beam deposition is used to fix the flake to the sample holder.

Since these operations are normally performed within the field of view of the focused ion beam system, the manipulator has low degree of freedom in operations. Thus, the flake taken out from an original sample is fixed to the sample holder at the same attitude (or in the same direction) as that is taken out. For example, since a semiconductor device has a wiring layer above and a substrate at the bottom, a flake from the semiconductor device is fixed to a sample base with the wiring layer thereabove.

The flake sample of the semiconductor device may further undergo a final process. Since the efficiency of etching with an ion beam is different in accordance with the materials of a wiring part, an interlayer insulating layer and a substrate, for example, some upper structures of samples may influence on the etching on the lower parts. For example, the influence of the upper structure may be significant in observing near a gate oxide film of a MOS transistor or observing the bottom of a via.

Accordingly, a technology has been disclosed that includes a focused ion beam system having a rotating mechanism that rotates a probe about the center axis thereof and a tilting mechanism that tilts the probe in the vertical direction about the probe as the center axis (see JP-A-2007-108105, FIG. 6).

According to the technology, a flake sample is fixed to the probe and is taken out from the original sample. Then, the probe is rotated about the center axis to invert the top-to-bottom direction of the sample. However, the probe is attached to the top surface of a sample holder at some angles. Thus, when the probe is rotated, the top surface of the sample and the top surface of the sample holder are not parallel. The tilting mechanism is used to tilt the probe so that the top surface of the sample and the top surface of the sample holder can be parallel. Then, the sample is moved to the sample holder and is fixed thereto. In this way, the lower part of the semiconductor device is turned upward such that a final process can be performed including irradiating an argon ion beam, for example, and removing a damaged layer of the sample.

However, the method using the probe having the rotating mechanism and the tilting mechanism may require a tilt angle of several tens degrees in accordance with the attached angles of the probe, and the tilting mechanism may be required to have a large stroke. However, it is difficult to provide the tilting mechanism in a narrow space near a sample within the focused ion beam system, which may increase the costs.

The invention was made in order to solve the problems, and it is an object of the invention to provide a focused ion beam system including microtweezers and a rotating mechanism therefor as manipulators so that the direction of a sample can be changed and the sample can be fixed to a sample holder, without requiring a tilting mechanism, and a sample processing method using the same.

SUMMARY OF THE INVENTION

In order to achieve the object, there is provided, according to an aspect of the invention, a focused ion beam system including a sample holder having a fixing plane for fixing a sample, a sample base on which the sample holder is provided, a focused ion beam irradiating mechanism that irradiates a focused ion beam to the sample, microtweezers that hold the sample and have the axial direction at a predetermined angle to a surface of the sample base, an opening/closing mechanism that opens and closes the microtweezers, a rotating mechanism that rotates the microtweezers about the axial direction, and a moving mechanism that moves the position of the microtweezers.

In this configuration, since the microtweezers are used to hold a sample, the work load can be reduced, without requiring deposition for holding the sample unlike the case using a probe.

When the fixing plane tilting toward the surface of the sample base is used, the microtweezers are only required to rotate about the axial direction in order to change the direction of the sample and make one surface of the sample and the fixing plane parallel. Thus, without requiring a tilting mechanism for the microtweezers, the direction of the sample can be changed, and the sample can be fixed directly to the fixing plane of the sample holder.

When the microtweezers holding the sample is rotated by a predetermined angle, the fixing plane may tilt toward the surface of the sample base such that one surface of the sample can be parallel with the fixing plane.

With the configuration, the microtweezers are only required to rotate about the axial direction in order to make one surface of the sample and the fixing plane parallel. Thus, the sample can be fixed directly to the fixing plane of the sample holder.

The focused ion beam system may further include a control portion that rotates the microtweezers holding the sample by a predetermined angle, moves the microtweezers so that the sample can be abutted against the fixing plane, and then moves the microtweezers such that one surface of the sample can be parallel with the fixing plane.

With the configuration, when a sample is abutted against the fixing plane and the microtweezers are then moved in a predetermined direction, force is applied to the sample on the fixing plane, and the direction of the sample changes. Then, one surface of the sample becomes parallel with the fixing plane. Thus, the direction of the sample can be changed, and, at the same time, the sample can be fixed to the fixing plane directly.

According to another aspect of the invention, there is provided a sample processing method using a focused ion beam system, the method using a focused ion beam to process a sample, the method including a holding step of holding a sample with microtweezers having the axial direction at a predetermined angle to a surface of a sample base, a rotating step of rotating the microtweezers holding the sample about the axial direction by a predetermined angle, and a fixing step of bringing the rotated microtweezers closer to a sample holder having a fixing plane for fixing the sample and fixing the sample to the fixing plane, wherein, when the rotating step rotates the microtweezers, the fixing plane tilts toward the surface of the sample base such that one surface of the sample can be parallel with the fixing plane.

According to another aspect of the invention, there is provided a sample processing method using a focused ion beam system, the method using a focused ion beam to process a sample, the method including a holding step of holding a sample with microtweezers having the axial direction at a predetermined angle to a surface of a sample base, a rotating step of rotating the microtweezers holding the sample about the axial direction by a predetermined angle, an abutting step of bringing the rotated microtweezers closer to a sample holder having a fixing plane for fixing the sample and abutting the sample against the fixing plane, and a moving step of, after abutting the sample against the fixing plane, moving the microtweezers such that one surface of the sample can be parallel with the fixing plane.

According to the invention, since, in processing with a focused ion beam system, microtweezers and a rotating mechanism therefor are used as manipulators, the direction of a sample can be changed, and the sample can be fixed to a sample holder, without requiring a tilting mechanism.

DETAILED DESCRIPTION OF THE PREFERRED EMBODIMENTS

With reference to drawings, embodiments of the invention will be described below.

Figure 1:
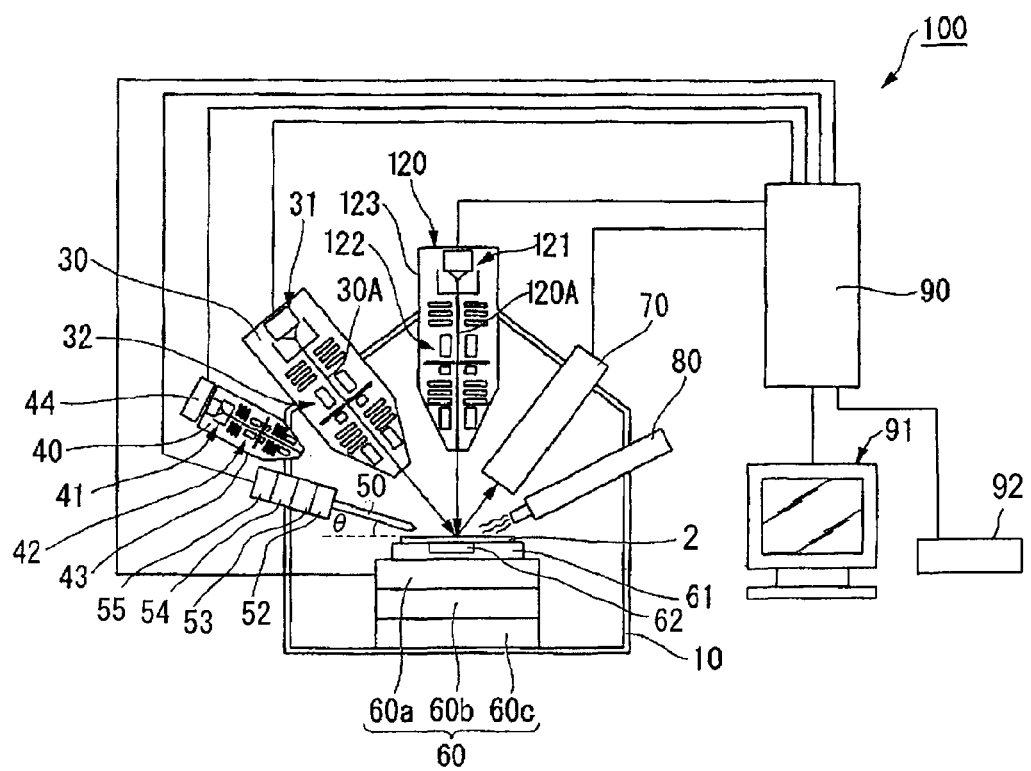
FIG. 1 is a block diagram illustrating the entire configuration of a focused ion beam system according to an embodiment of the invention.

FIG. 1 is a block diagram illustrating the entire configuration of a focused ion beam system 100 according to an embodiment of the invention. Referring to FIG. 1, the focused ion beam system 100 includes a vacuum chamber 10, an ion beam irradiating system (which corresponds to a "focused ion beam irradiating mechanism" according to an embodiment of the invention) 120, an electron beam irradiating system 30, an argon ion beam irradiating system 40, microtweezers 50, a sample stage 60, a secondary charged particle detector 70, a gas gun 80, and a control portion 90. The interior of the vacuum chamber 10 is depressurized to a predetermined degree of vacuum, and a part or all of the components of the focused ion beam system 100 are placed within the vacuum chamber 10.

The sample stage 60 supports a disk-shaped sample base 61 movably, and an original sample 2 such as a semiconductor wafer is mounted on the sample base 61. The sample stage 60 has a moving mechanism that displaces the sample base 61 on five axes. The moving mechanism includes an XYZ moving mechanism 60b that moves the sample base 61 along an X-axis and a Y-axis, which are parallel with the horizontal plane and orthogonal to each other, and along a Z-axis, which is orthogonal to the X-axis and Y-axis, a rotating mechanism 60c that rotates the sample base 61 about the Z-axis, and a tilting mechanism 60a that rotates the sample base 61 about the X-axis (or Y-axis). The sample stage 60 displaces the sample base 61 on five axes so that the original sample can be moved to the irradiation position of an ion beam 120A.

Here, the ion beam 120A is irradiated to etch the original sample 2, and a sample piece for a transmission electron microscope (TEM), which will be called TEM sample, is thus produced. After that, the sample piece is held with the microtweezers 50 and is moved to a sample holder 62 for TEM observation, and TEM observation is performed thereon. The sample holder 62 is placed along the circumference of the sample base 61. The sample piece taken out from the original sample 2 and held by the microtweezers 50 corresponds to a "sample" according to an embodiment of the invention.

The microtweezers 50 have two pointed ends and have a rear end supported by a tweezers holder 52. The microtweezers 50 are attached to the tweezers holder 52 with the axial direction at a predetermined angle θ to the surface of the sample base 61. This is because, if the microtweezers 50 are not attached diagonally to the surface of the sample base 61, it is difficult to hold the sample piece etched from the original sample 2 on the sample base 61 with the microtweezers 50. However, when the axial direction of the microtweezers 50 is at a right angle to the surface of the sample base 61, the rotation of the microtweezers 50, as will be described later, does not invert the top-to-bottom direction of the sample piece. Thus, $0° < \theta < 90°$ is assumed.

The rear end of the tweezers holder 52 is connected to an opening/closing mechanism 53. The opening/closing mechanism 53 opens and closes the pointed ends of the microtweezers 50 so as to hold or release a sample piece. The microtweezers 50 may be produced by a semiconductor silicon processing technology such as MEMS. Two proximate needles may be opened and closed by using the opening/closing mechanism 53 (such as a static actuator) so that they can function as tweezers. When voltage is applied to the static actuator, the interval between the two needles increases. When voltage is cancelled, the elastic force recovers the interval between the needles.

The rear end of the opening/closing mechanism 53 is supported by a rotating mechanism 54. The rotating mechanism 54 may include a stepping motor, for example, and the microtweezers 50 attached to the opening/closing mechanism 53 and tweezers holder 52 can be rotated about the axial direction (Z-axis). The rear end of the rotating mechanism 54 is connected to a moving mechanism 55. The moving mechanism 55 moves the tweezers holder 52 along the X-axis and Y-axis, which are parallel with a horizontal plane and are orthogonal to each other, and along the Z-axis orthogonal to the X-axis and Y-axis. The moving mechanism 55 may include a piezo actuator, for example.

According to the invention, the moving mechanism 55 is not required to include a tilting mechanism that further rotates the tweezers holder 52 about the X-axis (or Y-axis). This is because, as will be described later, according to the invention, when the rotating mechanism 54 only rotates the tweezers holder 52 (or microtweezers 50) about the axial direction, the direction of the sample can be changed, and the sample can thus be fixed to the sample base. This can eliminate the necessity for a tilting mechanism having large strokes of tilt angles of the order of several tens degrees in accordance with the attaching angles of the microtweezers 50. Furthermore, the tilting mechanism is not required to arrange in a narrow space within the focused ion beam system. The omission of the tilting mechanism can reduce the costs.

Since the microtweezers 50 are used to hold a sample and the deposition of a sample is thus not required unlike the case using a probe, the work load can be reduced.

The control portion 90 may be configured by a computer including a CPU (or central processing unit), a storage unit (such as a RAM and a ROM) 93 that stores data and/or programs, and an input port and output port for inputting and outputting a signal to and from an external apparatus. In the control portion 90, the CPU performs arithmetic processing on the basis of programs stored in the storage unit 93 so as to control the components in the focused ion beam system 100. The control portion 90 is electrically connected to the control wiring and the like for the focused ion beam (which will sometimes just be called "ion beam") irradiating system 20, electron beam irradiating system 30, argon ion beam irradiating system 40, microtweezers 50, secondary charged particle detector 70 and sample stage 60.

The control portion 90 further converts the secondary charged particles detected by the secondary charged particle detector 70 to a luminance signal, thus creates image data representing a sample surface and creates the sample image on the basis of the image data. The sample image is output to the display apparatus 91 connected to the control portion 90.

The control portion 90 further drives the sample stage 60 on the basis of a software instruction or operator's input and adjusts the position or attitude of an original sample so as to adjust the irradiation position and/or irradiation angle of the ion beam 120A to the original sample surface. The control portion 90 further drives the rotating mechanism 54, moving mechanism 55 and opening/closing mechanism 53 so as to adjust the position and/or attitude of the microtweezers 50 and grasp the sample piece with the microtweezers 50.

The control portion 90 is connected to input means 92 such as a keyboard for acquiring an instruction input by an operator.

The ion beam irradiating system 120 includes an ion source 121 that generates ions and an ion optical system 122 that forms the ions outflowing from the ion source 121 into a focused ion beam and scans the focused ion beam. The ion beam 120A being a charged particle beam is irradiated from the ion beam irradiating system 120 including an ion beam tube 23 to the original sample 2 on the sample stage 60 within the vacuum chamber 10. Here, from the original sample 2, secondary charged particles such as secondary ions and secondary electrons are generated. The secondary charged particles are detected by the secondary charged particle detector 70, and an image of the original sample 2 is acquired. The ion beam irradiating system 120 may increase the amount of irradiation of the ion beam 120A so as to perform etching processing on the original sample in the irradiation range.

The ion optical system 122 may include, for example, a condenser lens that focuses the ion beam 120A, an aperture that narrows the ion beam 120A, an aligner that adjusts the optical axis of the ion beam 120A, an objective lens that focuses the ion beam 120A to a sample, and a deflector that scans the ion beam 120A on the sample.

The electron beam irradiating system 30 includes an electron source 31 that emits electrons and an electron-optical system 32 that forms the electrons emitted from the electron source 31 into a beam and scans the beam. Due to the irradiation of the electron beam 30A emitted from the electron beam irradiating system 30 to an original sample, the original sample generates secondary electrons. The generated secondary electrons may be detected by the secondary charged particle detector 70 to acquire an image of the original sample or a sample piece thereof. Here, the electron beam 30A emitted from the electron beam tube 33 is irradiated onto the original sample at the same irradiation position as that of the ion beam 120A.

In this way, according to the invention, in order to acquire a sample image rendering a sample surface, the secondary charged particles (such as secondary ions and secondary electrons) generated by the irradiation of the ion beam 120A may be used, or the secondary charged particles (such as secondary electrons) generated by the irradiation of the electron beam 30A may be used. According to the invention, charged particle beam equipment without the electron beam irradiating system 30 may be used.

The argon ion beam irradiating system 40 includes an argon ion source 41, an argon ion optical system 42, and an argon ion beam tube 43 and further includes beam-position control means 44 for controlling the irradiation position of an argon ion beam. The argon ion beam irradiating system 40 irradiates an argon ion beam for cleaning the original sample 2.

When the ion beam 120A or electron beam 30A is irradiated to the original sample 2, the secondary charged particle detector 70 detects the secondary charged particles (such as secondary electrons and secondary ions) generated from the original sample.

The gas gun 80 emits a predetermined kind of gas such as etching gas to an original sample. Supplying etching gas by the gas gun 80 and at the same time irradiating the ion beam 120A to the original sample 2 can increase the speed of etching the sample with the ion beam 120A. Furthermore, supplying compound gas by the gas gun 80 and at the same time irradiating the ion beam 120A to an original sample allow deposition of a local gas component near the area with the irradiation of the ion beam 120A.

Figure 2:
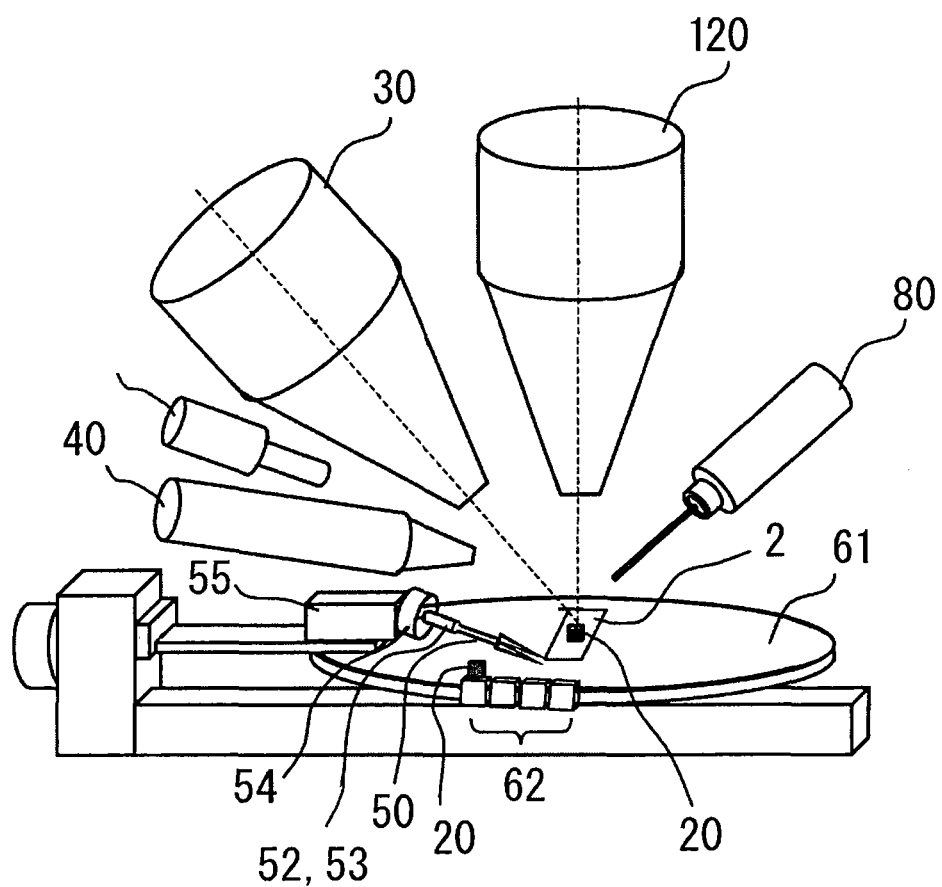
FIG. 2 is an enlarged view illustrating a structure within the focused ion beam system near a sample base.

FIG. 2 is an enlarged view illustrating a structure within the focused ion beam system near the sample base 61. The original sample 2 is mounted at the center of the sample base 61 and is etched with the ion beam 120A. As a result, a TEM sample piece 20 is produced. After that, the sample piece 20 is held with the microtweezers 50, is brought closer to the sample holder 62 by the moving mechanism 55, is rotated by the rotating mechanism 54, which will be described later, and then is fixed to the sample holder 62. The sample piece 20 may be fixed to the sample holder 62 by ion beam deposition, for example.

Figure 3:
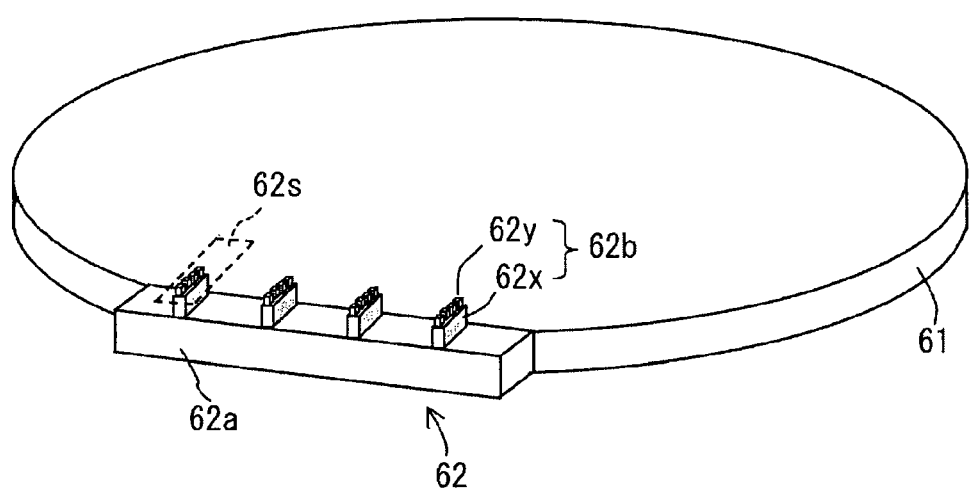
FIG. 3 is a diagram illustrating an example of the configuration of a sample holder.

FIG. 3 is a diagram illustrating an example of the configuration of the sample holder 62. The sample holder 62 includes a long and narrow parallelepiped enclosure 62a and four holder portions 62b arranged in the longitudinal direction on the top surface of the enclosure 62a. Each of the holder portions 62b includes a substantially semicircular mesh portion 62x containing molybdenum, for example, and a sample attachment 62y containing silicon, for example, connected to the surface of the flat part of the mesh portion 62x. The sample attachment 62y has plural (four or five) bars projecting upward. The bars are aligned in the planar direction of the holder portion 62b. A sample piece is to be fixed to the pointed ends of the bars. The semicircular part of the mesh portion 62x is buried in the enclosure 62a, and the flat part is parallel with the top surface of the enclosure 62a.

In the sample holder 62, the side surface adjacent to the top surface of the enclosure 62a is connected to a side wall of the sample base 61, and the top surface of the enclosure 62a is parallel with the sample base 61. Thus, the plane (which will be called fixing plane and also corresponds to a "fixing plane" according to an embodiment of the invention) 62s extending along the pointed ends of the bars of the sample attachment 62y that fixes a sample piece is also parallel with the sample base 61. Notably, the planar direction of the holder portion 62b corresponds to the radial direction of the sample base 61. A sample piece may be attached to a side surface of the sample attachment 62y, for example in the embodiments that will be described later.

In this way, the sample holder 62 having the fixing plane 62s parallel with the sample base 61 is preferably used in a sample processing method according to a third embodiment of the invention.

Figure 4:
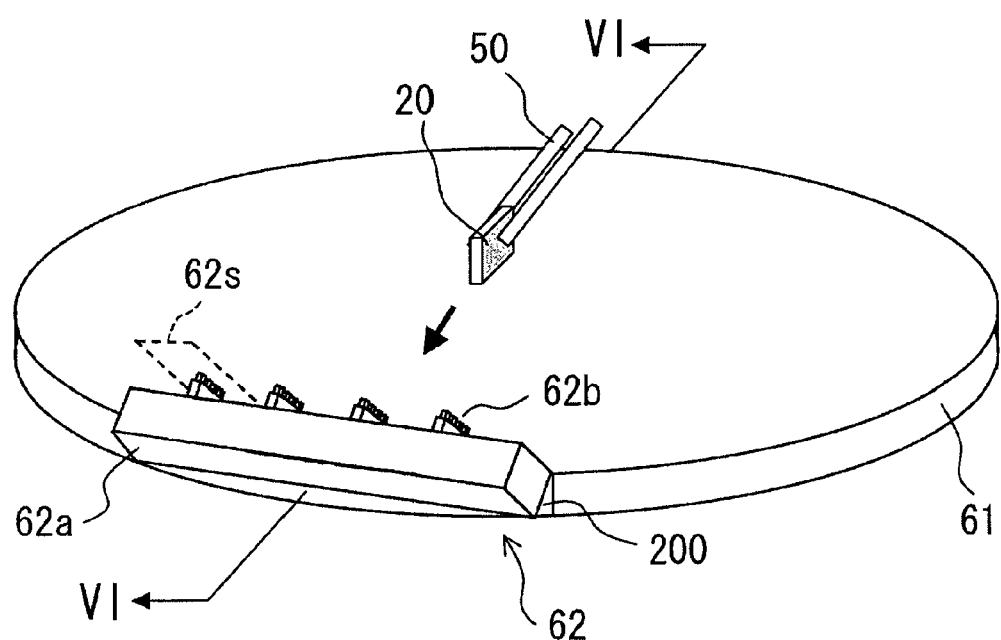
FIG. 4 is a diagram illustrating an example where the sample holder is tilted toward and is attached to the sample base.

FIG. 4 is a diagram illustrating an example where the sample holder 62 is tilted toward and is attached to the sample base 61. A spacer 200 having a wedge-shaped cross-section is mounted between a side surface of the enclosure 62a of the sample holder 62 and a side wall of the sample base 61. The top surface of the enclosure 62a tilts downward to the center of the sample base 61. Thus, the fixing plane 62s tilts downward to the center of the sample base 61 about the surface of the sample base 61

In this way, the sample holder 62 having the fixing plane 62s tilting toward the sample base 61 is applicable to the sample processing method of the first embodiment of the invention. In the sample processing method of the first embodiment of the invention, when the microtweezers 50 holding the sample piece 20 are rotated, one surface of the sample piece 20 is parallel with the fixing plane 62s.

Figure 5:
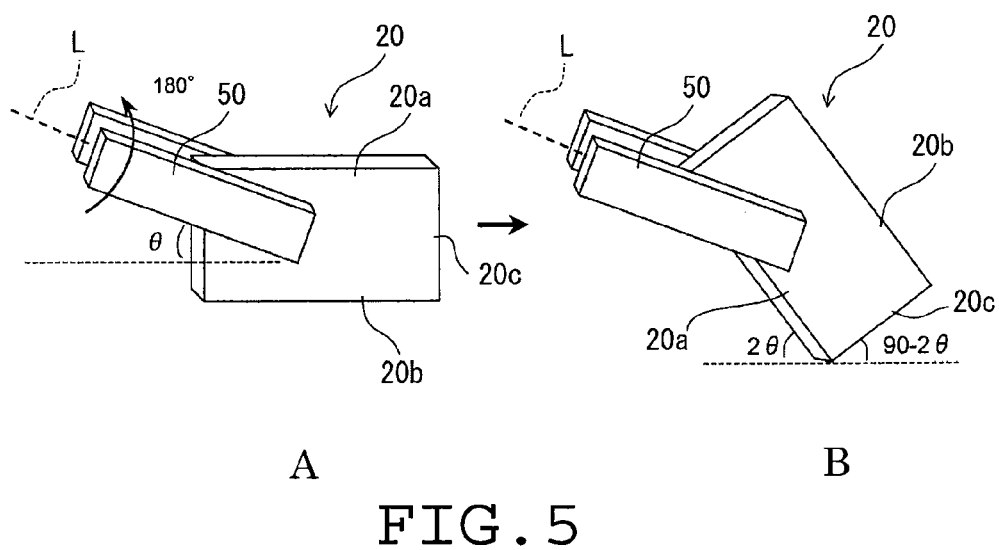
FIGS. 5A and 5B illustrate a holding step of holding a sample piece with microtweezers and a rotating step of rotating the microtweezers holding the sample piece by a predetermined angle.

FIGS. 5A and 5B illustrate, in a sample processing method of the first embodiment of the invention, a holding step (in FIG. 5A) of holding the sample piece 20 with the microtweezers 50 and a rotating step (in FIG. 5B) of rotating the microtweezers 50 holding the sample piece 20 by a predetermined angle (such as 180°).

The axial direction L of the microtweezers 50 and the surface of the sample base 61 form a predetermined angle (θ). The rectangular sample piece 20 rises perpendicularly from the surface of the sample base 61, the top side 20a (and bottom side 20b) of the sample piece 20 and L for an angle θ. Thus, when the holding step holds the sample piece 20, the top surface (and bottom surface) of the sample piece 20 and the axial direction L form the angle θ.

On the other hand, when the rotating step rotates the microtweezers 50 by 180°, the top-to-bottom direction of the sample piece 20 is inverted, and the bottom side 20b is positioned above. Because of the complementary relationship, the top side 20a and the surface of the sample base 61 for the angle 2θ, and the side 20c (which is the side adjacent to the top side 20a) of the sample piece 20 and the surface of the sample base 61 form the angle (90-2θ).

Figure 6:
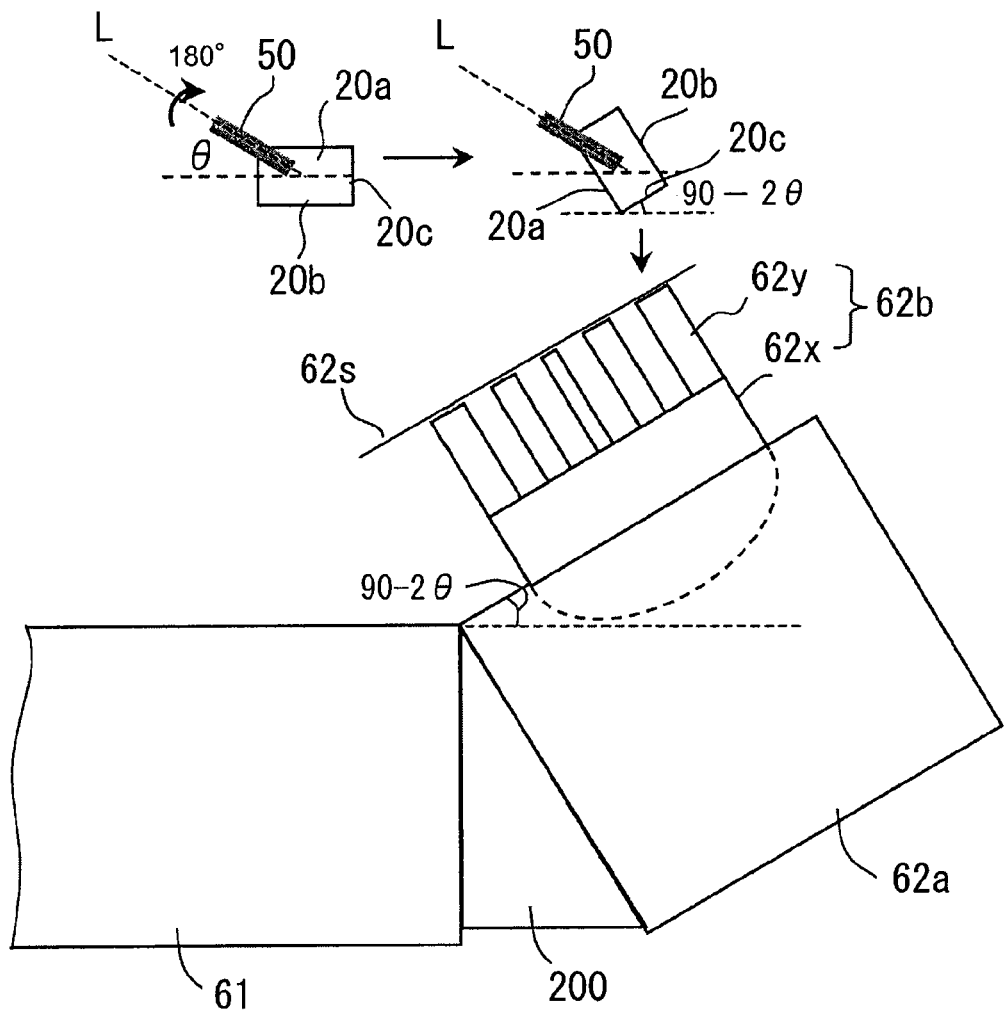
FIG. 6 is a section view taken on the line VI-VI in FIG. 4.

FIG. 6 is a section view taken on the line VI-VI in FIG. 4. With reference to FIG. 6, there will be described a fixing step of rotating the microtweezers 50 holding the sample piece 20 and fixing the sample piece to the fixing plane 62s of the sample holder 62.

When the sample piece 20 is held with the microtweezers 50, the bottom side 20b of the sample piece 20 faces downward, and the side 20c positions on the pointed-end side. When the microtweezers 50 are rotated about the axial direction L by 180°, the side 20c of the sample piece 20 forms the angle (90-2θ) with the surface of the sample base 61 and faces downward.

Here, since the top surface of the enclosure 62a of the sample holder 62 tilts by the angle (90-2θ) toward the surface of the sample base 61, the fixing plane 62s also tilts by the angle (90-2θ) toward the surface of the sample base 61. Thus, the side 20c of the sample piece 20 (which corresponds to "one surface of the sample" according to an embodiment of the invention where, more accurately, the end face of the side 20c corresponds to the "one surface") is parallel with the fixing plane 62s, and the sample piece 20 can be fixed to the fixing plane 62s directly.

In other words, rotating the microtweezers 50 may only be required to change the direction of the sample and fix the sample to the sample base, without tilting the attaching angle of the microtweezers 50.

Figure 7:
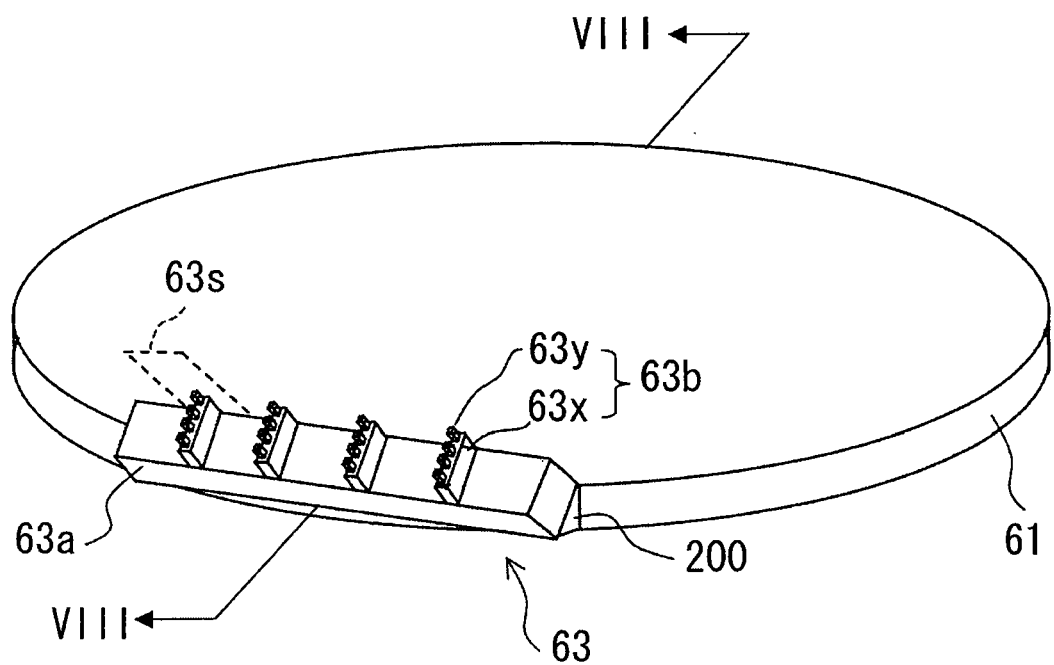
FIG. 7 is a diagram illustrating another example where a sample holder is tilted toward and is attached to the sample base.

FIG. 7 is a diagram illustrating another example where a sample holder 63 to be used in the sample processing method of the first embodiment of the invention is tilted toward and is attached to the sample base 61.

The same spacer 200 having a wedge-shaped cross-section as that in FIG. 4 is provided between the side surface of the enclosure 63a of the sample holder 63 and the side wall of the sample base 61. The top surface of the enclosure 63a tilts downward to the center of the sample base 61. However, the sample holder 63 is different from the sample holder 62 in that holder portions 63b thereof are buried in the outside surface of the enclosure 63a.

In the case of the sample holder 63, the side of the bars of a sample attachment 63y is a fixing plane 63s for fixing the sample piece 20. Therefore, the fixing plane 63s tilts downward to the center of the sample base 61.

Figure 8:
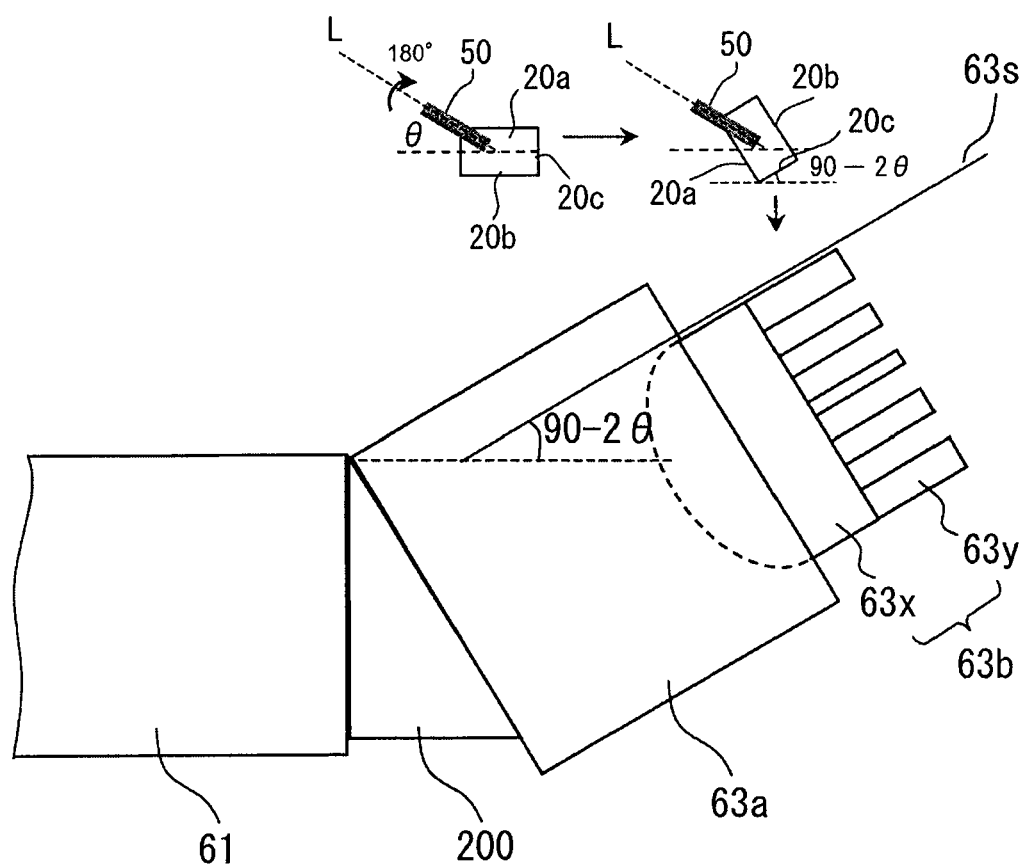
FIG. 8 is a section view taken on the line VIII-VIII in FIG. 7.

FIG. 8 is a section view taken on the line VIII-VIII in FIG. 7. With reference to FIG. 8, there will be described a fixing step of rotating the microtweezers 50 holding the sample piece 20 and fixing the sample piece to the fixing plane 63s of the sample holder 63.

Like the case in FIG. 6, when the sample piece 20 is held with the microtweezers 50, the bottom side 20b of the sample piece 20 faces downward, and the side 20c positions on the pointed-end side. When the microtweezers 50 are rotated about the axial direction L by 180°, the side 20c of the sample piece 20 forms the angle (90-2θ) with the surface of the sample base 61 and faces downward.

Here, since the top surface of the enclosure 63a of the sample holder 62 tilts by the angle (90-2θ) toward the surface of the sample base 61, the fixing plane 63s also tilts by the angle (90-2θ) toward the surface of the sample base 61. Thus, the side 20c of the sample piece 20 is parallel with the fixing plane 63s, and the sample piece 20 can be fixed to the fixing plane 63s directly. In other words, rotating the microtweezers 50 may only be required to change the direction of the sample and fix the sample to the sample base, without tilting the attaching angle of the microtweezers 50.

In the case of the sample holder 63, the sample piece 20 is fixed to the side of the bars of the sample attachment 63y. Thus, when the sample holder 63 is returned to the horizontal state to observe the sample piece 20, the sample piece 20 can be observed from a different direction from that of the sample holder 62.

Figure 9A:
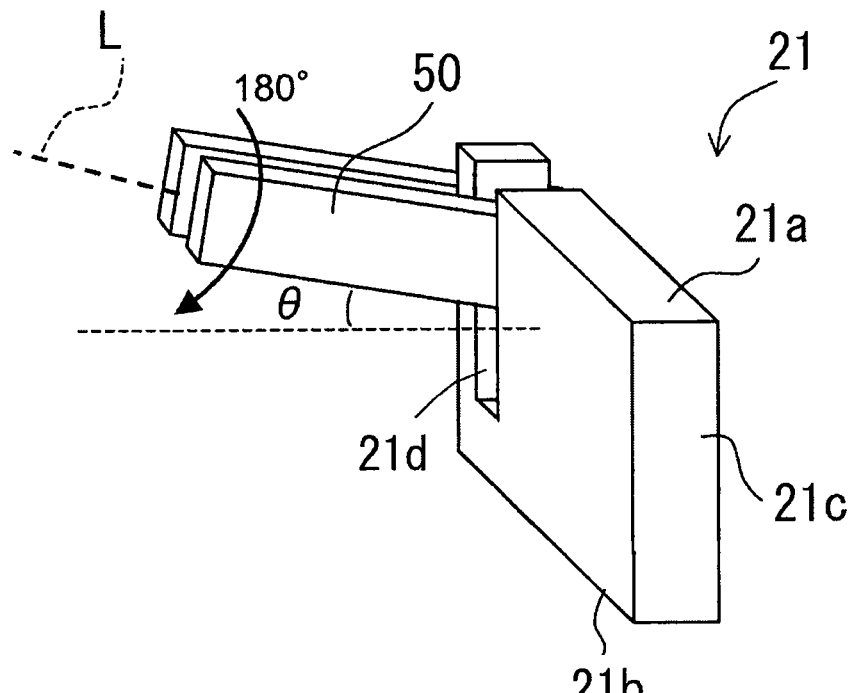
FIGS. 9A and 9B are another diagrams illustrate a holding step of holding a sample piece with the microtweezers and a rotating step of rotating the microtweezers holding the sample piece by a predetermined angle.
Figure 9B:
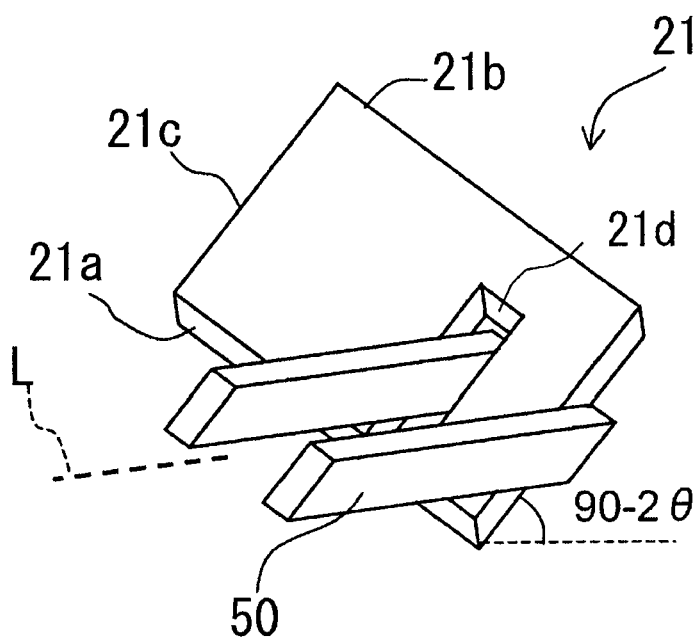

FIGS. 9A and 9B illustrate, in a sample processing method of a second embodiment of the invention, a holding step (in FIG. 9A) of holding a sample piece 21 with the microtweezers 50 and a rotating step (in FIG. 9B) of rotating the microtweezers 50 holding the sample piece 21 by a predetermined angle (such as 180°).

According to the second embodiment, a cut 21d is provided from the top side 20a to the bottom side 20b of the sample piece 21, and the part between the cut 21d and a side of the sample piece 21 is held with the microtweezers 50.

The axial direction L of the microtweezers 50 and the surface of the sample base 61 form a predetermined angle (θ). The rectangular surface of the sample piece 21 and the axial direction L form the angle θ.

On the other hand, when the rotating step rotates the microtweezers 50 by 180°, the top-to-bottom direction of the sample piece 21 is inverted, and the bottom side 21b is positioned above. Because of the complementary relationship, the surface of the sample piece 21 forms the angle (90-2θ) with the surface of the sample base 61.

Figure 10:
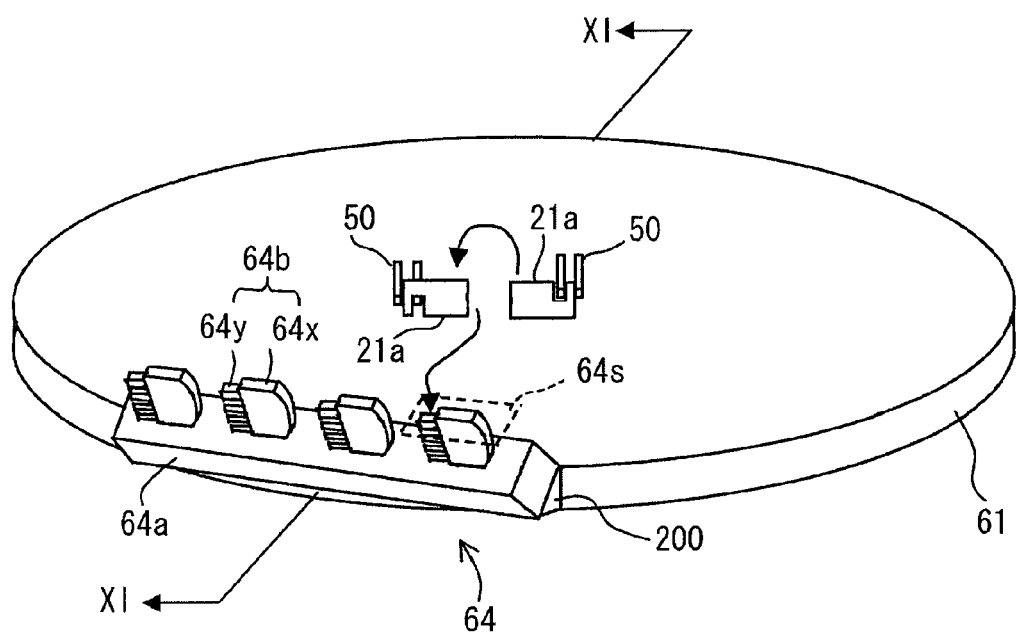
FIG. 10 is a diagram illustrating another example where the sample holder is tilted toward and is attached to the sample base.

FIG. 10 is a diagram illustrating an example where a sample holder 64 to be used in the sample processing method of the second embodiment of the invention is tilted toward and is attached to the sample base 61. The sample holder 64 has a holder portion 64b instead of the holder portion 63b in FIG. 7. The planar direction of the holder portion 64b is orthogonal to the outside surface of the enclosure 64a and extends along the longitudinal direction of the enclosure 64a, and the holder portion 64b is arranged such that the direction of the alignment of the bars of sample attachments 64y can also be orthogonal to the outside surface of the enclosure 64a. Since the other characteristics are the same as those of the sample holder 63, the description on the same parts will be omitted.

In the case of the sample holder 64, a side of the bars of each of the sample attachments 64y is a fixing plane 64s for fixing the sample piece 21. Thus, the fixing plane 64s tilts upward to the center of the sample base 61.

Figure 11:
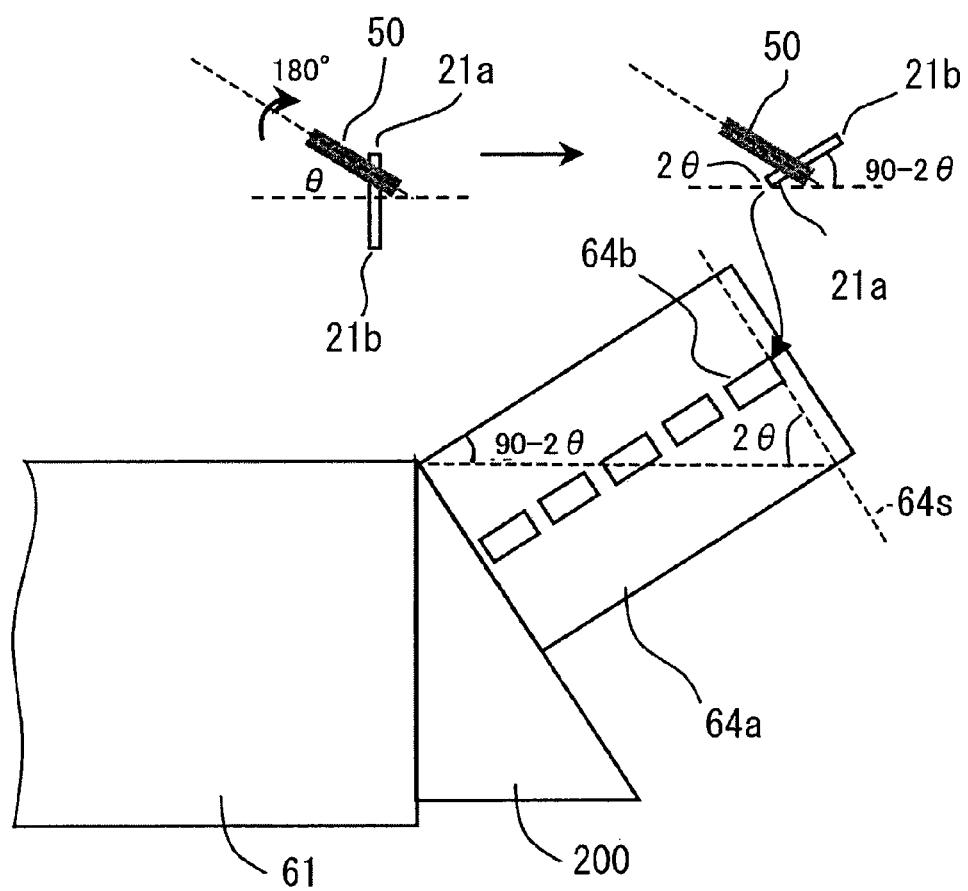
FIG. 11 is a section view taken on the line XI-XI in FIG. 10.

FIG. 11 is a section view taken on the line XI-XI in FIG. 10. With reference to FIG. 11, there will be described a fixing step of rotating the microtweezers 50 holding the sample piece 21 and fixing the sample piece to the fixing plane 64s of the sample holder 64.

When the sample piece 21 is held with the microtweezers 50, the top side 21a of the sample piece 21 faces upward. When the microtweezers 50 are rotated about the axial direction L by 180°, the top side 21a of the sample piece 21 faces downward, and the surface of the sample piece 21 forms the angle (90-2θ) with the surface of the sample base 61. The end face of the upper side 21a forms the angle 2θ with the surface of the sample base 61 (since the end face of the top side 21a is at a right angle to the surface of the sample piece 21).

On the other hand, the top surface of the enclosure 64a of the sample holder 64 tilts toward the surface of the sample base 61 by the angle (90-2θ), and the fixing plane 64s is perpendicular to the top surface of the enclosure 64a. Thus, the fixing plane 64s tilts toward the surface of the sample base 61 by 2θ. Therefore, (the end face of) the top side 21a of the sample piece 21 is parallel with the fixing plane 64s, and the top side 21a of the sample piece 21 can be fixed to the fixing plane 64s directly. In other words, rotating the microtweezers 50 may only be required to change the direction of the sample and fix the sample to the sample base, without tilting the attaching angle of the microtweezers 50.

Figure 12:
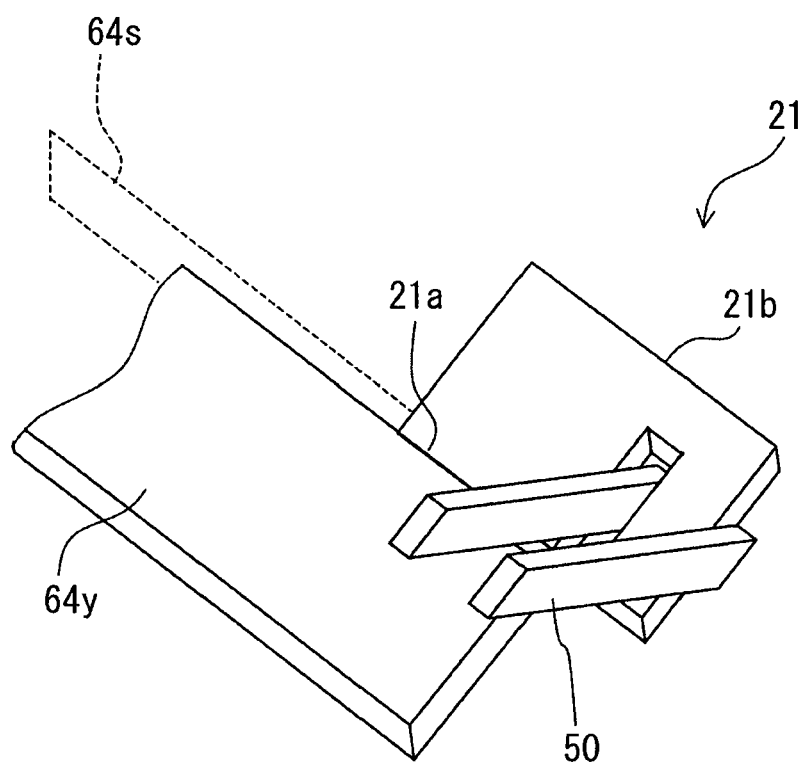
FIG. 12 is a diagram illustrating the state that a sample piece is fixed to the fixing plane.

FIG. 12 illustrates the state that the sample piece 21 is fixed to the fixing plane 64s. The microtweezers 50 are rotated, and the top side 21a of the sample piece 21 is fixed to the fixing plane 64s. Thus, the top side 21a of the sample piece 21 is attached to the sides of the bars of the sample attachment 64y.

Figure 13:
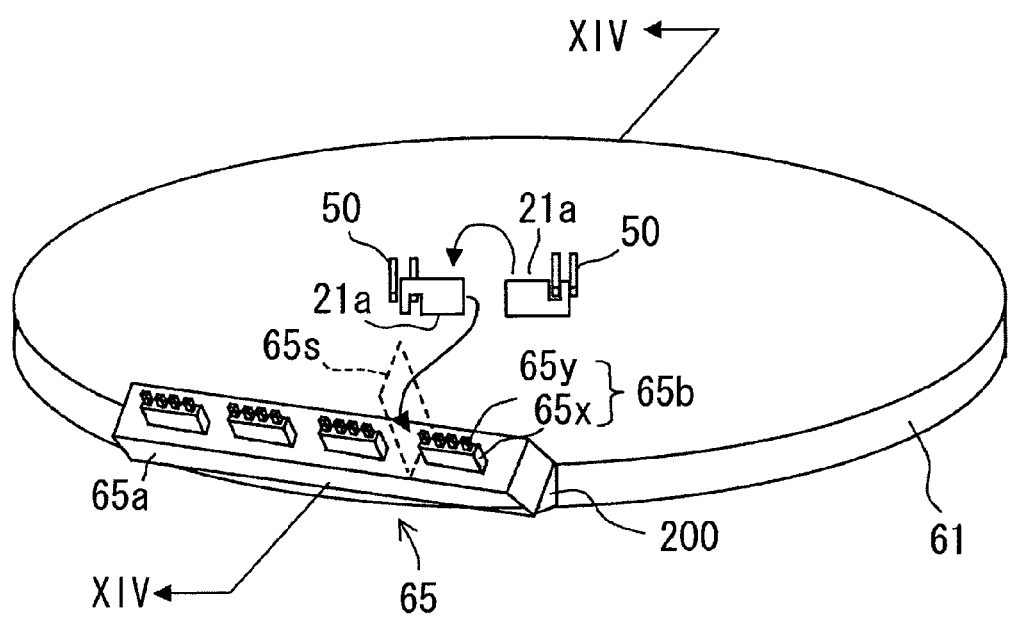
FIG. 13 is a diagram illustrating another example where the sample holder is tilted toward and is attached to the sample base.

FIG. 13 is a diagram illustrating another example where a sample holder 65 to be used in the sample processing method of the second embodiment of the invention is tilted toward and is attached to the sample base 61. Since the sample holder 65 is similar to the sample holder 63 except that a holder portion 65b is the holder portion 63b in FIG. 7 rotated on a surface of the enclosure 65a by 90°, the description on the same parts will be omitted.

In the case of the sample holder 65, the plane which is on a side of the bars of each of sample attachments 65y and orthogonal to the plane of the sample holder 65 is a fixing plane 65s for fixing the sample piece 21. Thus, the fixing plane 65s is perpendicular to the surface of the sample base 61. The side of the bars tilts downward to the center of the sample base 61.

Figure 14:
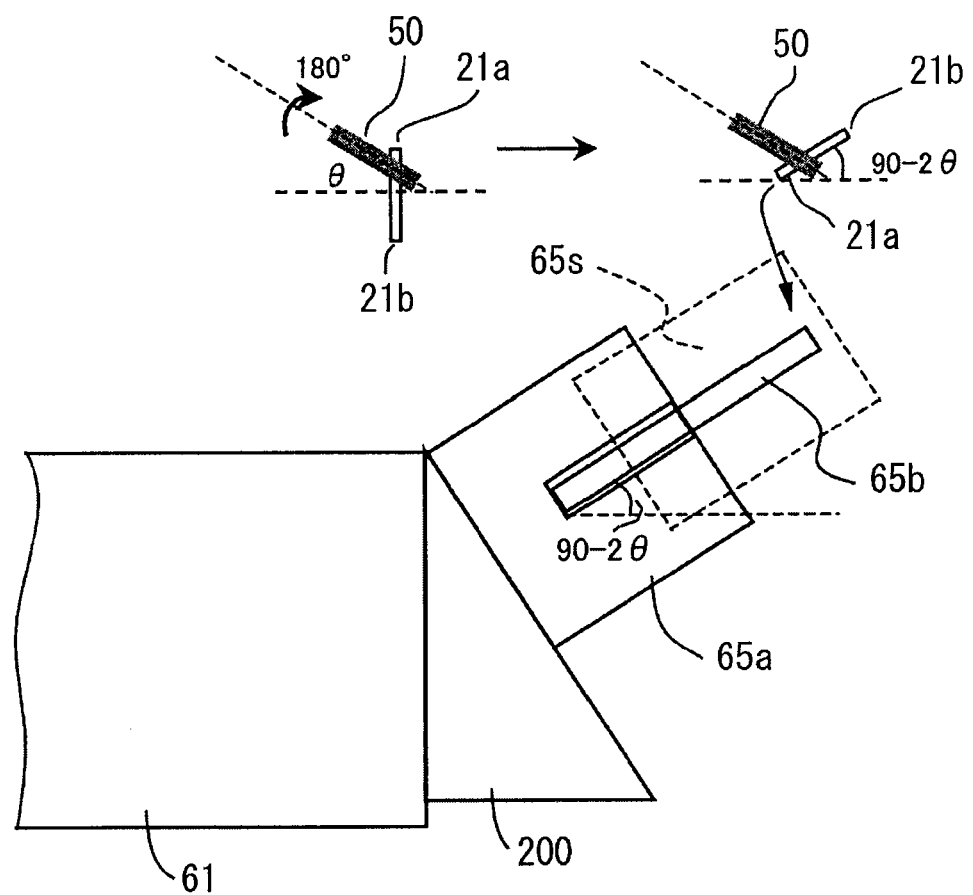
FIG. 14 is a section view taken on the line XIV-XIV in FIG. 13.

FIG. 14 is a section view taken on the line XIV-XIV in FIG. 13. With reference to FIG. 14, there will be described a fixing step of rotating the microtweezers 50 holding the sample piece 21 and fixing the sample piece 21 to the fixing plane 65s.

When the sample piece 21 is held with the microtweezers 50, the bottom side 21b of the sample piece 21 faces downward. When the microtweezers 50 is rotated about the axial direction L by 180°, the bottom side 21b of the sample piece 21 faces upward, and the surface of the sample piece 21 forms the angle (90-2θ) with a surface of the sample base 61.

In the example in FIG. 14, since the fixing plane 65s is perpendicular to the surface of the sample base 61, (the end face of) the side 21c of the sample piece 21 is parallel with the fixing plane 65s, without rotating the microtweezers 50. However, when the microtweezers 50 are rotated, the direction that the bars of the sample attachment 65y on the fixing plane 65s extend is parallel with the direction that the side 21c extends (more specifically, the direction that the bars extend forms the angle (90-2θ) with the surface of the sample base 61). Thus, the sample piece 21 can be fixed to the fixing plane 65s.

Figure 15:
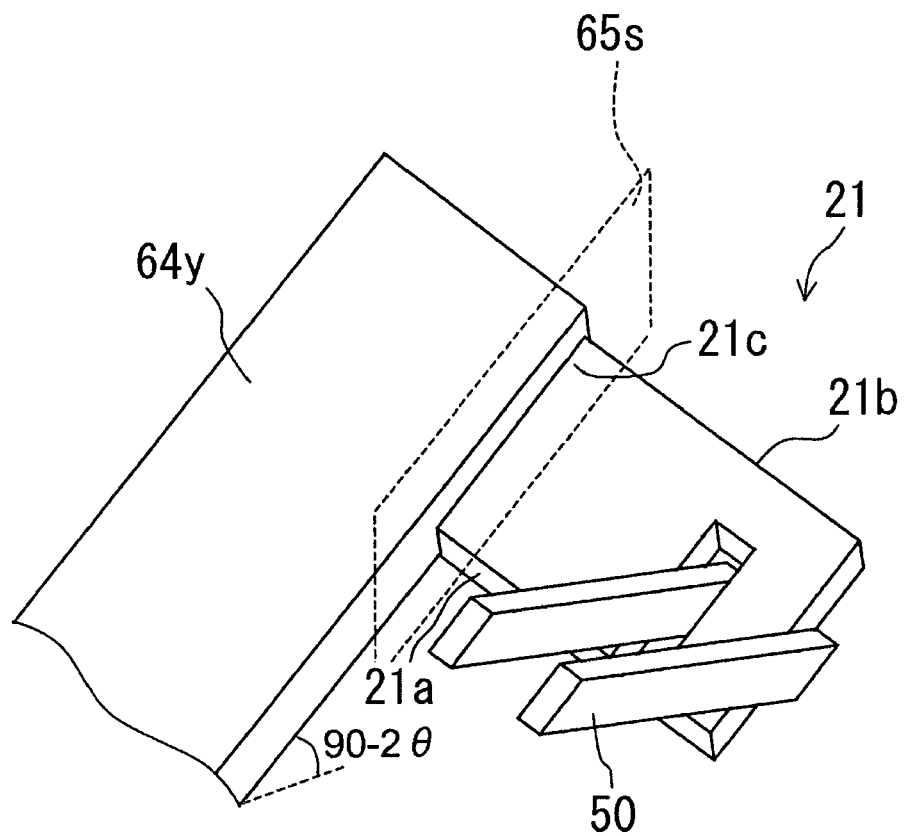
FIG. 15 is another diagram illustrating state that a sample piece is fixed to the fixing plane.

FIG. 15 illustrates the state that the sample piece 21 is fixed to the fixing plane 65s. The microtweezers 50 are rotated, and the side 21c of the sample piece 21 is fixed to the fixing plane 65s. Thus, the side 21c of the sample piece 21 is attached along the side of the bars of the sample attachment 64y.

Figures 16A, 16B:
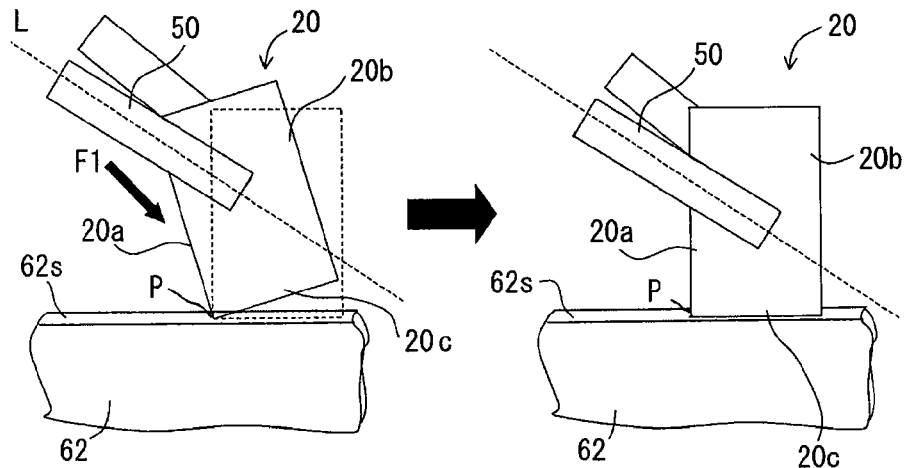
FIGS. 16A and 16B are a process chart illustrating a sample processing method of a third embodiment of the invention.

FIGS. 16A and 16B are a process chart illustrating a sample processing method of a third embodiment of the invention. First of all, the microtweezers 50 are used to hold the sample piece 20. Since the holding step is exactly the same as that in FIG. 5A, the illustration will be omitted. Next, the microtweezers 50 holding the sample piece 20 is rotated by a predetermined angle (such as 180°), and the top-to-bottom direction of the sample is inverted. Since the rotating step is exactly the same as that in FIG. 5B, the illustration will be omitted. The sample processing method of the third embodiment uses the sample holder 62 (which is a normal sample holder) having the fixing plane 62s parallel with the sample base 61, as illustrated in FIG. 3.

Next, the rotated microtweezers 50 are brought closer to the sample holder 62, and the sample piece 20 is abutted against the fixing plane 62s of the sample holder 62 (abutting step/FIG. 16A).

Here, the axial direction L of the microtweezers 50 originally forms an angle θ with the sample base 61 (as in FIG. 5A), (the end face of) the side 20c of the sample piece 20 is not parallel with the fixing plane 62s, and the corner P of the side 20c is only hooked (or abutted) on the fixing plane 62s.

Then, when the microtweezers 50 are moved to a front direction F1, the side 20c falls to the front about the corner P being the fulcrum point, and (the end face of) the side 20c faces in parallel with the fixing plane 62s so that the side 20c can be attached to the fixing plane 62s (moving step/FIG. 16B). Therefore, rotating the microtweezers 50 may only be required to change the direction of the sample and fix the sample to the sample base, without tilting the attaching angle of the microtweezers 50.

In order to easily move the side 20c about the corner P being the fulcrum point, the corner P of the sample piece 20 may be abutted against the fixing plane 62 as in FIG. 16A, and then the side 20c may be moved by gradually reducing the holding force by the microtweezers 50.

Figures 17A, 17B:
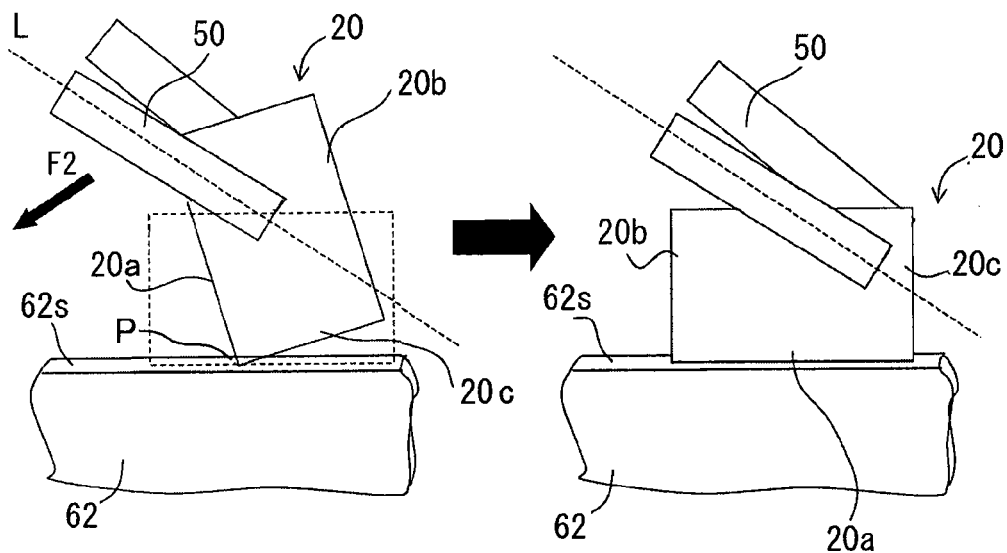
FIGS. 17A and 17B are a process chart illustrating another sample processing method of the third embodiment of the invention

FIGS. 17A and 17B are a process chart illustrating another sample processing method of the third embodiment of the invention. Since the holding step and rotating step before the abutting step in FIG. 17A are exactly the same as those in FIGS. 5A and 5B, the illustration and the description will be omitted.

The example in FIGS. 17A and 17B is different from the example in FIGS. 16A and 16B in that, after the abutting step in FIG. 17A hooks (or abuts) the corner P of the side 20c on the fixing plane 62s, the microtweezers 50 are moved to a rear direction F2, and the top side 20a is tilted rearward about the corner P being the fulcrum point.

Thus, (the end face of) the top side 20a faces in parallel with the fixing plane 62s, and the top side 20a can be attached to the fixing plane 62s (by the moving step/FIG. 17B). Therefore, rotating the microtweezers 50 may only be required to change the direction of the sample and fix the sample to the sample base, without tilting the attaching angle of the microtweezers 50.

The invention is not limited to the embodiments but includes various changes and equivalents without departing from the spirit and scope of the invention.

For example, according to the embodiments, the sample holder is tilted toward the sample base, and the fixing plane provided on the sample holder is tilted toward the surface of the sample base. However, the fixing plane may be diagonally attached within the sample holder, and the sample holder itself may be attached to the sample base in parallel. However, a normal sample holder has the fixing plane in parallel with (or at a right angle to) the enclosure of the sample holder. For that reason, the embodiment in which a spacer is provided between the normal sample holder and the sample base to adjust the angle is more preferable because a generic sample holder can be used therefor.

According to the embodiments, the sample holder is a mesh having aligned thin bars. However, the invention is not limited thereto, but a semicircular mesh (which fixes a sample to a flat part thereof) having been used in the past may be used instead. The sample is not limited to the TEM sample piece.

According to the sample processing method of the third embodiment, an operator manually performs the processing. However, the control portion 90 may cause a computer to implement the sample processing method of the third embodiment.

In this case, the control portion 90 first acquires the position of the sample piece 20 (by image processing, for example), moves the microtweezers 50 to the position and then controls so as to open the microtweezers 50. Next, the control portion 90 closes the microtweezers 50 to hold the sample piece 20 (which is the holding step). If the control portion 90 determines that the sample piece 20 has been held, the rotating mechanism rotates the microtweezers 50 (which is the rotating step). The control portion 90 acquires in advance the coordinates of the fixing plane 62s of the sample holder 62, moves the microtweezers 50 and moves the held sample piece 20 to the coordinates. Thus, the sample piece 20 is abutted against the fixing plane 62s (which is the abutting step).

When the sample piece 20 is abutted against the fixing plane 62s, a predetermined force of impact is detected through the microtweezers 50. By using it as a key, the control portion 90 moves the microtweezers 50 to a predetermined direction (such as the direction F1 or F2 in FIG. 16A and FIG. 17B). Thus, since one surface of the sample piece 20 faces in parallel with the fixing plane 62s, the control portion 90 controls so as to perform deposition on the fixing part and fix the sample piece 20 to the fixing plane 62s. After that, the control portion 90 controls so as to open and move the microtweezers 50, and the processing ends.

What is claimed is:

1. A focused ion beam system comprising:
    a sample base having a side surface;
    a sample holder comprising a top surface having an enclosure for receiving a sample and a side surface movably attached to the side surface of the sample base, wherein the sample holder is arranged in one of a horizontal state where the top surface of the sample holder is parallel to a top surface of the sample base and a tilting state where the top surface of the sample holder is not parallel to the top surface of the sample base;
    a focused ion beam irradiating mechanism that irradiates a focused ion beam to the sample;
    microtweezers for holding the sample in an axial direction which forms a predetermined angle to a surface of the sample base;
    a control portion in communication with the sample holder and the microtweezers and operable to execute instructions that control movements of the microtweezers and the sample holder, wherein the instructions, upon execution by the control portion:
    cause the microtweezers holding the sample to rotate by a predetermined angle; and
    cause the sample holder to tilt the top surface of the sample holder toward a top surface of the sample base such that one surface of the sample can be parallel with the enclosure arranged on the top surface of the sample holder.

2. The focused ion beam system according to claim 1, wherein the control portion is operable to further execute instructions that cause the microtweezers to place the sample in the enclosure arranged on the top surface of the sample holder and the sample holder to return to the horizontal state.

3. A sample processing method using a focused ion beam system, the method using a focused ion beam to process a sample, the method comprising:
   a holding step of holding a sample with microtweezers in an axial direction which forms a predetermined angle to a surface of a sample base;
   a rotating step of rotating the microtweezers holding a sample about the axial direction by a predetermined angle; and
   a fixing step of bringing the rotated microtweezers closer to a sample holder, wherein the sample holder is movably attached on a sidewall of the sample base and includes a fixing plane for fixing the sample, wherein:
   the fixing step further comprises:
      tilting the fixing plane of the sample holder toward the surface of the sample base such that one surface of the sample is arranged to be parallel with the fixing plane of the sample holder; and
      tilting back the fixing plane of the sample holder to be parallel with the surface of the sample base.

4. A sample processing method using a focused ion beam system, the method using a focused ion beam to process a sample, the method comprising:
   a holding step of holding a sample with microtweezers in an axial direction which forms a predetermined angle to a surface of a sample base;
   a rotating step of rotating the microtweezers holding the sample about the axial direction by a predetermined angle;
   an abutting step of bringing the rotated microtweezers closer to a sample holder, wherein the sample holder is movably attached on a sidewall of the sample base and has a fixing plane, the abutting step abutting the sample against the fixing plane of the sample holder; and
   a moving step of, after abutting the sample against the fixing plane of the sample holder, moving the microtweezers and the sample holder such that one surface of the sample can be parallel with the fixing plane of the sample holder, the moving step further comprising:
   tilting the fixing plane of the sample holder toward the surface of the sample base such that one surface of the sample is arranged to be parallel with the fixing plane of the sample holder and tilting back the fixing plane of the sample holder to be parallel with the surface of the sample base.

* * * * *